US009775350B2

(12) United States Patent
Zhang et al.

(10) Patent No.: US 9,775,350 B2
(45) Date of Patent: *Oct. 3, 2017

(54) MICRONIZED WOOD PRESERVATIVE FORMULATIONS IN ORGANIC CARRIERS

(75) Inventors: Jun Zhang, Gertzville, NY (US); Robert M. Leach, Grand Island, NY (US)

(73) Assignee: Koppers Performance Chemicals Inc., Pittsburgh, PA (US)

(*) Notice: Subject to any disclaimer, the term of this patent is extended or adjusted under 35 U.S.C. 154(b) by 883 days.

This patent is subject to a terminal disclaimer.

(21) Appl. No.: 13/161,772

(22) Filed: Jun. 16, 2011

(65) Prior Publication Data

US 2011/0250358 A1 Oct. 13, 2011

Related U.S. Application Data

(63) Continuation of application No. 11/243,640, filed on Oct. 5, 2005, now abandoned.

(60) Provisional application No. 60/618,729, filed on Oct. 14, 2004.

(51) Int. Cl.

| | | |
|---|---|---|
| *A01N 59/20* | (2006.01) |
| *A01N 43/653* | (2006.01) |
| *A01N 53/00* | (2006.01) |
| *A01N 51/00* | (2006.01) |
| *A01N 47/18* | (2006.01) |
| *A01N 47/12* | (2006.01) |
| *A01N 47/04* | (2006.01) |
| *A01N 47/02* | (2006.01) |
| *A01N 43/80* | (2006.01) |
| *A01N 43/78* | (2006.01) |
| *A01N 43/42* | (2006.01) |
| *A01N 37/34* | (2006.01) |
| *A01N 33/12* | (2006.01) |
| *A01N 25/04* | (2006.01) |
| *B27K 3/00* | (2006.01) |
| *B27K 3/22* | (2006.01) |
| *B27K 3/34* | (2006.01) |
| *B27K 3/52* | (2006.01) |
| *C09D 5/14* | (2006.01) |

(52) U.S. Cl.
CPC ........... *A01N 43/653* (2013.01); *A01N 59/20* (2013.01); *C09D 5/14* (2013.01); *B27K 3/005* (2013.01); *B27K 3/22* (2013.01); *B27K 3/343* (2013.01); *B27K 3/52* (2013.01)

(58) Field of Classification Search
CPC ...... A01N 59/20; A01N 43/653; A01N 53/00; A01N 51/00; A01N 47/18; A01N 47/12; A01N 47/04; A01N 47/02; A01N 43/80; A01N 43/78; A01N 43/42; A01N 37/34; A01N 33/12; A01N 25/04; B27K 3/005; B27K 3/22; B27K 3/343; B27K 3/52; C09D 5/14

See application file for complete search history.

(56) References Cited

U.S. PATENT DOCUMENTS

| | | |
|---|---|---|
| 1,388,513 A | 8/1921 | Chandler |
| 1,999,458 A | 4/1935 | Hollister |
| 2,558,304 A | 6/1951 | Marcot et al. |
| 3,007,844 A | 11/1961 | Schulz |
| 3,087,936 A | 4/1963 | Le Suer et al. |
| 3,231,464 A | 1/1966 | Dettwiler et al. |
| 3,254,025 A | 5/1966 | Le Suer et al. |
| 3,321,464 A | 5/1967 | Oberley |
| 3,443,881 A | 5/1969 | Hudson |
| 3,535,423 A | 10/1970 | Ordas |
| 3,622,377 A | 11/1971 | Conner |
| 3,816,307 A | 6/1974 | Woods |
| 3,837,875 A | 9/1974 | Murphy |
| 3,874,891 A | 4/1975 | Grobmann et al. |
| 3,945,835 A | 3/1976 | Clarke et al. |
| 3,957,494 A | 5/1976 | Oberley |
| 3,968,276 A | 7/1976 | Allen |
| 4,003,994 A | 1/1977 | Downer et al. |
| 4,058,607 A | 11/1977 | Hennart et al. |
| 4,061,770 A | 12/1977 | Marks |
| 4,062,991 A | 12/1977 | Kyte et al. |
| 4,075,325 A | 2/1978 | Kauzal |
| 4,075,326 A | 2/1978 | Kuyama et al. |
| 4,089,999 A | 5/1978 | Mondt et al. |
| 4,142,009 A | 2/1979 | Kyte et al. |
| 4,172,904 A | 10/1979 | Young et al. |
| 4,220,688 A | 9/1980 | Mitchell et al. |

(Continued)

FOREIGN PATENT DOCUMENTS

| | | |
|---|---|---|
| AU | B-15117/92 | 10/1992 |
| AU | 646732 B2 | 3/1994 |

(Continued)

OTHER PUBLICATIONS

Patent Owner's Response Under 37 CFR 1.951(a) to the Action Closing Prosecution in Inter Partes Reexamination Control No. 95/001,418. May 27, 2011.
Declaration of Dr. John N.R. Ruddick Under 37 CFR 1.132, in Inter Partes Reexamination Control No. 95/001,418. May 26, 2011.
Backman, P.A., et al., "The Effects of Particle Size and Distribution on Performance of the Fungicide Chlorothalonil, Phytopathology," St. Paul, MD, US, vol. 66, No. 10, 1 Jan. 1, 1976, pp. 1242-1245, XP009062911.
Supplementary European Search Report for PCT/US2005/016503 dated Feb. 2, 2009.
Supplementary European Search Report for PCT/US2005/037303 dated Feb. 5, 2009.

(Continued)

*Primary Examiner* — John Pak
*Assistant Examiner* — Nathan W Schlientz
(74) *Attorney, Agent, or Firm* — Covington & Burling LLP

(57) ABSTRACT

Provided is a composition for the preservation of wood and other cellulosic materials. The composition comprises a dispersion of micronized inorganic compounds and/or organic biocides in an organic carrier. Also provided is a method for making the composition.

13 Claims, 2 Drawing Sheets

(56) References Cited

U.S. PATENT DOCUMENTS

| | | |
|---|---|---|
| 4,310,590 A | 1/1982 | Petigara |
| 4,313,976 A | 2/1982 | Leach |
| 4,339,617 A | 7/1982 | Imai et al. |
| 4,404,169 A | 9/1983 | Ploss et al. |
| RE31,576 E | 5/1984 | Hilditch |
| 4,456,486 A | 6/1984 | Bernhard |
| 4,507,152 A | 3/1985 | Collins et al. |
| 4,539,047 A | 9/1985 | Crockatt et al. |
| 4,596,694 A | 6/1986 | Rozmus |
| 4,597,730 A | 7/1986 | Rozmus |
| 4,622,248 A | 11/1986 | Leach et al. |
| RE32,329 E | 1/1987 | Paszner |
| 4,649,065 A | 3/1987 | Hein et al. |
| 4,650,792 A | 3/1987 | Underwood |
| 4,663,364 A | 5/1987 | Iwasaki et al. |
| 4,670,430 A | 6/1987 | Imamura et al. |
| 4,698,099 A | 10/1987 | Nakamura et al. |
| 4,702,776 A | 10/1987 | Hoffner et al. |
| 4,720,514 A | 1/1988 | Needham |
| 4,737,491 A | 4/1988 | Leppavuori et al. |
| 4,741,971 A | 5/1988 | Beck et al. |
| 4,752,297 A | 6/1988 | Leach |
| 4,808,406 A | 2/1989 | Brinkman |
| 4,857,214 A | 8/1989 | Papay et al. |
| 4,857,365 A | 8/1989 | Hirao et al. |
| 4,872,916 A | 10/1989 | Latosky |
| 4,897,427 A | 1/1990 | Barnavon et al. |
| 4,923,894 A | 5/1990 | Kanda et al. |
| 4,950,221 A | 8/1990 | Gordon |
| 4,961,865 A | 10/1990 | Pennartz |
| 4,986,851 A | 1/1991 | Dietz et al. |
| 4,988,545 A | 1/1991 | Laks |
| 5,030,285 A | 7/1991 | Vallvey et al. |
| 5,049,677 A | 9/1991 | Prout et al. |
| 5,098,472 A | 3/1992 | Watkins et al. |
| 5,110,822 A | 5/1992 | Sherba et al. |
| 5,130,463 A | 7/1992 | Haubennestel et al. |
| 5,145,684 A | 9/1992 | Liversidge et al. |
| 5,147,686 A | 9/1992 | Ichimura et al. |
| 5,151,218 A | 9/1992 | Haubennestel et al. |
| 5,186,947 A | 2/1993 | Goettsche et al. |
| 5,196,407 A | 3/1993 | Goletz et al. |
| 5,198,133 A | 3/1993 | Papay |
| 5,200,421 A | 4/1993 | Ludwig et al. |
| 5,207,823 A | 5/1993 | Shiozawa |
| 5,277,979 A | 1/1994 | Kielbania, Jr. et al. |
| 5,304,376 A | 4/1994 | Friedrichs et al. |
| 5,342,438 A | 8/1994 | West |
| 5,360,783 A | 11/1994 | Itoh et al. |
| 5,424,077 A | 6/1995 | Lajoie |
| 5,426,121 A | 6/1995 | Bell |
| 5,438,034 A | 8/1995 | Walker |
| 5,462,589 A | 10/1995 | Nicholas et al. |
| 5,462,931 A | 10/1995 | Shaber et al. |
| 5,470,585 A | 11/1995 | Gilchrist |
| 5,478,598 A | 12/1995 | Shiozawa |
| 5,484,934 A | 1/1996 | Ikeda et al. |
| 5,527,384 A | 6/1996 | Williams et al. |
| 5,527,423 A | 6/1996 | Neville et al. |
| 5,527,816 A | 6/1996 | Shaber et al. |
| 5,536,305 A | 7/1996 | Yu |
| 5,552,378 A | 9/1996 | Trinh et al. |
| 5,582,638 A | 12/1996 | Coutelle et al. |
| 5,624,916 A | 4/1997 | Shaber et al. |
| 5,635,217 A | 6/1997 | Goettsche et al. |
| 5,667,795 A | 9/1997 | Fraley et al. |
| 5,714,507 A | 2/1998 | Valcke et al. |
| 5,763,364 A | 6/1998 | Frisch et al. |
| 5,833,741 A | 11/1998 | Walker |
| 5,855,662 A | 1/1999 | Brand et al. |
| 5,874,025 A | 2/1999 | Heuer et al. |
| 5,874,456 A | 2/1999 | McDade |
| 5,874,476 A | 2/1999 | Hsu et al. |
| 5,879,025 A | 3/1999 | Blumenthal |
| 5,916,356 A | 6/1999 | Williams et al. |
| 5,961,843 A | 10/1999 | Hayakawa et al. |
| 5,972,266 A | 10/1999 | Fookes et al. |
| 5,990,043 A | 11/1999 | Kugler et al. |
| 6,033,648 A | 3/2000 | Candau |
| 6,074,986 A | 6/2000 | Mulqueen et al. |
| 6,110,263 A | 8/2000 | Goettsche et al. |
| 6,123,756 A | 9/2000 | Poppen et al. |
| 6,139,879 A | 10/2000 | Taylor |
| 6,143,318 A | 11/2000 | Gilchrist et al. |
| 6,250,350 B1 | 6/2001 | Muraki et al. |
| 6,274,199 B1 | 8/2001 | Preston et al. |
| 6,303,183 B1 | 10/2001 | Wilczynski et al. |
| 6,306,201 B1 | 10/2001 | Makino |
| 6,306,202 B1 * | 10/2001 | West .................. 106/18.3 |
| 6,306,939 B1 | 10/2001 | Gupta et al. |
| 6,342,556 B1 | 1/2002 | Batdorf et al. |
| 6,352,583 B1 | 3/2002 | Goettsche et al. |
| 6,471,976 B1 | 10/2002 | Taylor et al. |
| 6,475,631 B1 | 11/2002 | Yamamoto et al. |
| 6,482,814 B1 | 11/2002 | Bath et al. |
| 6,485,790 B2 | 11/2002 | Walker et al. |
| 6,503,306 B1 | 1/2003 | Watkins |
| 6,514,512 B1 | 2/2003 | Puterka et al. |
| 6,521,288 B2 | 2/2003 | Laks et al. |
| 6,537,670 B1 | 3/2003 | Sassi |
| 6,541,038 B1 * | 4/2003 | Tanaka et al. ............ 424/618 |
| 6,558,685 B1 | 5/2003 | Kober et al. |
| 6,572,788 B2 | 6/2003 | Walker |
| 6,576,661 B1 | 6/2003 | Bruck et al. |
| 6,579,354 B1 | 6/2003 | West |
| 6,585,989 B2 | 7/2003 | Herbst et al. |
| 6,593,260 B2 | 7/2003 | Nomura |
| 6,596,246 B2 | 7/2003 | Huato et al. |
| 6,646,147 B2 | 11/2003 | Richardson et al. |
| 6,686,056 B2 | 2/2004 | Roos et al. |
| 6,689,731 B2 | 2/2004 | Esselborn et al. |
| 6,699,818 B1 | 3/2004 | Walter et al. |
| 6,700,006 B2 | 3/2004 | Thames et al. |
| 6,753,035 B2 | 6/2004 | Laks et al. |
| 6,770,674 B1 | 8/2004 | Young |
| 6,830,822 B2 | 12/2004 | Yadav |
| 6,843,837 B2 | 1/2005 | Zhang et al. |
| 6,849,276 B1 | 2/2005 | Dufau et al. |
| 6,867,250 B1 | 3/2005 | Gupta et al. |
| 6,887,400 B1 | 5/2005 | Wei et al. |
| 6,905,531 B2 | 6/2005 | Richardson et al. |
| 6,905,532 B2 | 6/2005 | Richardson et al. |
| 7,105,136 B2 | 9/2006 | Ploss et al. |
| 7,238,654 B2 | 7/2007 | Hodge et al. |
| 7,316,738 B2 | 1/2008 | Richardson et al. |
| 7,426,948 B2 | 9/2008 | Richardson et al. |
| 7,449,130 B2 | 11/2008 | Lloyd et al. |
| 7,674,481 B2 * | 3/2010 | Leach et al. .............. 424/630 |
| 8,158,208 B2 | 4/2012 | Richardson et al. |
| 2001/0021711 A1 | 9/2001 | Beilfuss et al. |
| 2001/0051175 A1 | 12/2001 | Strom et al. |
| 2002/0003179 A1 | 1/2002 | Verhoff et al. |
| 2002/0047058 A1 | 4/2002 | Verhoff et al. |
| 2002/0051892 A1 | 5/2002 | Laks et al. |
| 2002/0055046 A1 | 5/2002 | Ono et al. |
| 2002/0110692 A1 | 8/2002 | Suzuki et al. |
| 2002/0128367 A1 | 9/2002 | Daisey et al. |
| 2003/0010956 A1 | 1/2003 | Las et al. |
| 2003/0013799 A1 | 1/2003 | Crooks et al. |
| 2003/0040569 A1 | 2/2003 | Curry et al. |
| 2003/0060504 A1 | 3/2003 | Yoshida et al. |
| 2003/0077219 A1 | 4/2003 | Ploss et al. |
| 2003/0086979 A1 | 5/2003 | Ghosh |
| 2003/0108759 A1 | 6/2003 | Roos et al. |
| 2003/0127023 A1 | 7/2003 | Grandidier et al. |
| 2003/0170317 A1 | 9/2003 | Curzon et al. |
| 2004/0024099 A1 | 2/2004 | Narayanan et al. |
| 2004/0050298 A1 | 3/2004 | Giger et al. |
| 2004/0051084 A1 | 3/2004 | Wessling et al. |
| 2004/0063847 A1 | 4/2004 | Curry et al. |
| 2004/0176477 A1 | 9/2004 | Davison et al. |
| 2004/0258767 A1 | 12/2004 | Leach et al. |
| 2004/0258768 A1 * | 12/2004 | Richardson et al. ......... 424/630 |
| 2004/0258838 A1 | 12/2004 | Richardson et al. |

(56) References Cited

U.S. PATENT DOCUMENTS

| | | |
|---|---|---|
| 2005/0013939 A1 | 1/2005 | Vinden et al. |
| 2005/0107467 A1 | 5/2005 | Richardson |
| 2005/0118280 A1 | 6/2005 | Leach et al. |
| 2005/0130866 A1 | 6/2005 | Richardson et al. |
| 2005/0152994 A1 | 7/2005 | Leach et al. |
| 2005/0182152 A1 | 8/2005 | Nonninger et al. |
| 2005/0249812 A1 | 11/2005 | Leach et al. |
| 2005/0252408 A1 | 11/2005 | Richardson et al. |
| 2005/0255251 A1* | 11/2005 | Hodge et al. .................. 427/397 |
| 2005/0256026 A1 | 11/2005 | Hodge et al. |
| 2005/0265893 A1 | 12/2005 | Leach et al. |
| 2006/0062926 A1 | 3/2006 | Richardson et al. |
| 2006/0075921 A1* | 4/2006 | Richardson et al. ...... 106/15.05 |
| 2006/0075923 A1 | 4/2006 | Richardson |
| 2006/0078686 A1 | 4/2006 | Hodge et al. |
| 2006/0086284 A1 | 4/2006 | Zhang et al. |
| 2006/0086841 A1 | 4/2006 | Richardson et al. |
| 2006/0112850 A1 | 6/2006 | Zhang et al. |
| 2006/0147632 A1 | 7/2006 | Zhang et al. |
| 2006/0257578 A1 | 11/2006 | Zhang et al. |
| 2006/0288904 A1 | 12/2006 | Leach et al. |
| 2007/0021385 A1 | 1/2007 | Zhang et al. |
| 2007/0131136 A1 | 6/2007 | Zhang et al. |
| 2007/0193473 A1 | 8/2007 | Zhang et al. |
| 2007/0259016 A1 | 11/2007 | Hodge et al. |
| 2008/0199525 A1 | 8/2008 | Leach et al. |
| 2008/0199535 A1 | 8/2008 | Taylor et al. |
| 2008/0210121 A1 | 9/2008 | Zhang et al. |
| 2008/0213608 A1 | 9/2008 | Richardson et al. |
| 2008/0260841 A1 | 10/2008 | Leach et al. |
| 2008/0286380 A1 | 11/2008 | Zhang et al. |
| 2009/0028917 A1 | 1/2009 | Leach et al. |
| 2009/0035564 A1 | 2/2009 | Leach et al. |
| 2009/0092683 A1 | 4/2009 | Leach et al. |
| 2009/0143478 A1 | 6/2009 | Richardson et al. |
| 2009/0280185 A1 | 11/2009 | Richardson et al. |

FOREIGN PATENT DOCUMENTS

| | | | |
|---|---|---|---|
| CA | 2251534 A1 | 10/1997 | |
| DE | 2531895 A1 | 2/1977 | |
| DE | 1531868 U | 11/1978 | |
| DE | 3542441 A1 | 6/1987 | |
| DE | 3930687 A1 | 4/1991 | |
| DE | 4112652 A1 | 10/1992 | |
| EP | 0173964 A2 | 3/1986 | |
| EP | 0256427 A2 | 2/1988 | |
| EP | 0472973 A1 | 3/1992 | |
| EP | 0499299 A2 | 8/1992 | |
| EP | 0577952 A1 | 1/1994 | |
| EP | 1034903 A1 | 9/2000 | |
| EP | 1649749 A1 | 4/2006 | |
| GB | 222268 A | 10/1924 | |
| GB | 812408 A | 4/1959 | |
| GB | 822869 A * | 11/1959 | ............. A01N 25/04 |
| GB | 822869 A1 | 11/1959 | |
| GB | 1491330 A | 11/1977 | |
| GB | 1531868 A | 11/1978 | |
| JP | S60-89422 | 4/1985 | |
| JP | 60-155403 A | 8/1985 | |
| JP | S61-246002 A * | 11/1986 | |
| JP | S62-39201 | 2/1987 | |
| JP | S62-116102 | 5/1987 | |
| JP | 01-026401 A | 1/1989 | |
| JP | 8-183010 A | 7/1996 | |
| JP | 10-272610 A | 10/1998 | |
| JP | 2000-102907 A | 4/2000 | |
| JP | 2000-141316 A | 5/2000 | |
| JP | 2001-121512 A | 5/2001 | |
| JP | 2003/266406 A | 9/2003 | |
| NZ | 225428 A | 3/1991 | |
| NZ | 280716 A | 2/1999 | |
| NZ | 304884 A | 3/1999 | |
| PL | 169344 | 5/1994 | |
| SE | 379167 B | 9/1975 | |
| SU | 0642166 A1 | 1/1979 | |
| WO | WO-85/00040 A1 | 1/1985 | |
| WO | WO-87/04696 A1 | 8/1987 | |
| WO | WO-92/19429 A1 | 11/1992 | |
| WO | WO-95/27600 A1 | 10/1995 | |
| WO | WO-98/05206 A1 | 2/1998 | |
| WO | WO-99/55505 | 11/1999 | |
| WO | WO-00/05955 A1 | 2/2000 | |
| WO | WO-00/24259 A1 | 5/2000 | |
| WO | WO-00/24528 A1 | 5/2000 | |
| WO | WO-00/60940 A1 | 10/2000 | |
| WO | WO-00/78281 A1 | 12/2000 | |
| WO | WO-02/00196 A2 | 1/2002 | |
| WO | WO-02/06417 A1 | 1/2002 | |
| WO | WO-03/025303 A1 | 3/2003 | |
| WO | WO-03/103392 A1 | 12/2003 | |
| WO | WO-2004/091875 A2 | 10/2004 | |
| WO | WO-2005/007368 A2 | 1/2005 | |
| WO | WO-2005/104841 A1 | 11/2005 | |
| WO | WO-2005/110692 A2 | 11/2005 | |
| WO | WO-2005/115704 A2 | 12/2005 | |
| WO | WO-2006/042128 A2 | 4/2006 | |
| WO | WO-2006/042129 A1 | 4/2006 | |

OTHER PUBLICATIONS

Koch, C.C., Synthesis of Nanostructured Materials by Mechanical Milling: Problems and Opportunities, NanoStructured Materials, vol. 9, pp. 13-22, 1997.

American Wood-Preservers' Association Standard E7-01, "Standard Method of Evaluating Preservatives by Filed Tests with Stakes," p. 1-9, 2006.

American Wood-Preservers' Association Standard E10-01, "Standard Method of Testing Wood Preservatives by Laboratory Soil-Block Cultures," p. 1-10, 2005.

The Merck Index (12th Ed. 1996) Merck & Co., Inc.

Davis, T. N., Food Storage and Preservative-Treated Wood, Alaska Science Forum, p. 1-2, Mar. 10, 1980 [online][retrieved on Mar. 19, 2009]. URL:http://www.gi.alaska.edu/ScienceForum/ASF3/380.htm/.

STN online, file SCISEARCH, Acc. No. 1993:540390 (Siegfried, Comparative Toxicity of Pyrethoid Insecticides to Terrestial and Aquatic Insects, Environmental Toxicology and Chemistry (1993), vol. 12, No. 9, pp. 1683-1689.

Superior Court of New Jersey, Decision After Trial, *Phibro-Tech, Inc.* v. *Osmose Holdings, Inc.*, p. 1-27, Jun. 25, 2007.

Superior Court of New Jersey, Chancery Division, Final Judgment, *Phibro-Tech, Inc.* v. *Osmose Holdings, Inc.*, Osmose, Inc., p. 1-3, Aug. 14, 2007.

Liu, Y., et al., Use of Nanoparticles for the Controlled Release of Biocides in Pressure-Treated Solid Wood, Polymer Preprints 38(2), 1997, pp. 624-625.

Liu, Y., et al., Michigan Technical Univ., Dept. of Chemistry, Houghton, MI, Use of Polymeric Nanoparticles for Controlled Release of Biocides in Solid Wood, Materials Research Society Symposium Proceedings Series; 1998, vol. 550, Abstract GG3.4.

Liu, Y., et al., "Use of Polymer Nanoparticles as Carriers for the Controlled release of Biocides in Solid Wood". Ph.D. Dissertation of Yong Liu; Michigan Technological University, Houghton, MI, 1999.

Liu, Y., et al., Use of Nanoparticles for Controlled Release of Biocides in Solid Wood, Journal of Applied Polymer Science, vol. 79, 2001, pp. 458-465.

Lide, Characteristics of Particles and Particles Dispersoids Handbook of Chemistry and Physics, 75th edition; 1994, Florida: CRC Press, pp. 15-38.

Shaw, www.fda.gov/ohmrms/dockets/ac/01/slides/3763s2_09_shaw.ppt; 2001.

International Society of Soil Science. (http://www.clays.org.au/mins.htm).

Lewis Sr., R. J., "Antineoplastic," Hawley's Condensed Chemical Disctionary, 14th Edition, John Wiley & Son, Inc., 2001, p. 86.

JP Published Unexamined Patent Application No. S61-246002 (Nov. 1, 1986).

(56) References Cited

OTHER PUBLICATIONS

JP Published Unexamined Patent Application No. S61-244502 (Oct. 30, 1986).
Schultz, T.P., et al., "A Brief Overview of Non-Arsenical Wood Preservative," American Chemical Society, Chapter 26, pp. 420-429, 2003.
S. E. A. McCallan, The Nature of the Fungicidal Action of Copper and Sulfur, The Botanical Review, pp. 629-643, Aug. 30, 1948.
M. Humar et al., "Influence of Moisture Content on EPR Parameters of Copper in Impregnated Wood," Holz als Roh-Und Werkstoff 59 (2001) 254-255.
M. Humar et al., Changes of the pH of impregnated Wood During Exposure to Wood-Rotting Fungi, Holz als Roh-und Werkstoff 59 (2001) 288-293.
A. Pizzi, "A New Approach to Non-Toxic, Wild-Spectrum, Ground-Contact Wood Preservatives. Pat I. Approach and Reaction Mechanisms," Holzforschung 47 (1993) 253-260.
A. Pizzi, "A New Approach to Non-Toxic, Wild-Spectrum, Ground-Contact Wood Preservatives. Pat II. Accelerated and Long-term Field Tests," Holzforschung 47 (1993) 343-348.
Stan Lebow, et al., "Fixation Effects on the Release of Copper, Chromium and Arsenic From CCA-C Treated Marine Piles, Report Prepared for American Wood-Preservers' Association Subcommitte P-3," Piles, Aug., 1999, pp. 168-174.
Izabela Ratajczak, et al., "Fixation of Copper (II)-Protein Formulation in Wood: Part 1. Influence of Tannic Acid on Fixation of Copper in Wood," Holzforschung, vol. 62, pp. 294-299, 2008.
S. N. Kartal, et al., "Do the Unique Properties of Nanometals Affect Leachability or Efficacy Against Fungi and Termines?" International Biodeterioration & Biodegradation 63 (2009) 490-495.
H. Kubel, et al., The Chemistry and Kinetic Behavior of Cu—Cr—As/B Wood Preservatives—Part Reactions of CCB and Cellulose, Lignin and their Simple Model Compounds, Holzforschung and Holzverwertung 34 (1982) 4, pp. 75-83.
A. Pizzi, et al., The Chemistry and Kinetic Behavior of Cu—Cr—As/B Wood Preservatives—Part Fixation of CCB in Wood and Physical and Chemical Comparison of CCB and CCA, Holzforschung and Holzverwertung 34 (1982) 5, pp. 80-86.
Raul A. Wapnir, Copper Absorption and Bioavailability, Am J Clin Nutr. 1998; 67 (suppl.): 1054S-60S.
Gadi Borkow, et al., Copper As A Biocidal Tool, Proceedings, ninety-Fifth Annual Meeting of the American Wood Preservers' Association, vol. 95, May 16-19, 1999.
H. S. Rathore, et al., Fungicide and Herbicide Residues in Water, Handbook of Water Analysis, pp. 608-654, Handbook of Water Analysis, 2000.
T.C. C Crusberg, et al., Biomineralization of Heavy Metals, pp. 409-417, 2004.
5.1 Inorganic Fungicides—5.1.1 Metal Salts, Pesticide Chemistry, pp. 272-486, 1988.
R. Thompson, CBE, The Chemistry of Wood Preservation, Feb. 28-Mar. 1, 1991.
H. M. Barnes, et al., The Impact of Test Site and Oil Content on the Performance of Pentachlorophenol-Treated Wood, Forest Products Journal, vol. 56, No. 5, pp. 43-47, May 2006.
J.J. Morrell, Wood Pole Maintenance Manual (1996 Edition), Research Contribution 15, Oct. 1996, p. 22.
Helmuth Rech, "Location of Pentachlorophenol by Electron Microscopy and Other Techniques in Cellon Treated Douglas-Fir," Forest Products J. 21/1, pp. 38-43, Jan. 1971.
M. Humar, et al., Effect of Oxalix, Acetic Acid, and Ammonia on Leaching of Cr and Cu From Preserved Wood, Wood Sci Technol 37 (2004) 463-473.
Cui, F. And Archer, K. J., "Treatment of lumber with preservative/water repellent emulsions—The significance of shear stability on penetration," The International Re-search Group on Wood Preservation, IRG/WP 97-20124, Paper prepared for the 28th Annual Meeting, Whistler, British Columbia, Canada (May 25-30, 1997).

Feist and Mraz, Forest Products Lab Madison Wis., Wood Finishing: Water Repellents and Water-Repellent Preservatives. Revision, Report Number-FSRN-FPL-0124-Rev ()NTIS 1978_.
Fojutowski, A.; Lewandowski, O., Zesz. Probl. Postepow Nauk Roln. No. 209: 197-204 (1978).
Hamilton, R.L. and Cosse, O. K., "Thermal Conductivity of Heterogenous Two-Component Systems," Ind. & Engr. Chem. Fund., 1, 187-191 (1962).
Laks, et al., "Polymer Nanoparticles as a Carrier System for Wood Preservatives," PowerPoint Presentation to Rohm & Haas under confidentiality agreement, Oct. 30, 1998 (even-numbered pages not available).
Nanotechnology in brief, Feb. 20, 2004, available at http://nanotechweb.org/articles/news/3/2/12/1.
Nasibulin Albert G., Ahonen, P. Petri, Richard, Richard, Olivier, Esko I, "Copper and Cooper Oxide Nanoparticle Formation by Chemical Vapor Nucleation From Copper (II) Acetylacetonate," Journal of Nanoparticles Research 3(5-6): 383-398 (2001).
Panshin AJ and De Zeeuw, Carl, Textbook of Wood Technology, 4th ed. pp. 112-113 (1980).
Supplementary European Search Report dated Apr. 21, 2009 for PCT/US2005/035946.
Bailey, Irving W., "The Preservative Treatment of Wood, II. The Structure of the Pit Membranes in the Tracheids of Conifers and their Relation to the Penetration of Gases, Liquids, and Finely Divided Solids into Green and Seasoned Wood," Forest Quarterly, 11:1220, p. 15 (1913).
Merriam-Webster's Collegiate Dictionary, 10th ed., 1993.
The Copper Champs! Unique Copper Hydroxide Formulations (Brochure), Nufarm Americas Inc. (2002).
Zahora, A. R. and Rector, C.M., "Water Repellent Additives for Pressure Treatments," Proceedings of the Eleventh Annual Meeting of the Canadian Wood Preservation Association, Toronto, Ontario, 11:22-41 (Nov. 6 and 7, 1990).
"Defendants' Answer to Plaintiffs Amended Complaint and Defendants' Counterclaims," Osmose, Inc. v. Arch Chemicals, et al., USDC, Eastern District of VA, Norfolk Division Case No. C.A. No. 2:10 cv 108-JBF/FBS, pp. 1-38, May 30, 2010.
"Osmose's Answer to Defendants' Counterclaims," Osmose, Inc. v. Arch Chemicals, et al., USDC, Eastern District of VA, Norfolk Division Case No. C.A. No. 2:10 cv 108-JBF/FBS, p. 1-13, Jun. 1, 2010.
"Defendants' Supplemental Response to Interrogatory No. 12 and its Subparts," Osmose, Inc. v. Arch Chemicals, et al., USDC, Eastern District of VA, Norfolk Division Case No. C.A. No. 2:10 cv 108-JBF.
Notice of Opposition to a European Patent (Application No. EP04776802.3/Patent No. EP1651401), filed by Dr. David Elsy on Apr. 21, 2010.
Statement of Grounds and Particulars filed by Arch Wood Protection Pty Ltd. with the Commissioner of Patents on Dec. 18, 2009, in the Matter of Australian Patent Application No. 2004230950 in the name of Osmose, Inc.
Rudd, et al. "The Influence of Ultraviolet Illumination on the Passive Behavior of Zinc," Journal of the Electrochemical Society, 147 (4) p. 1401-1407, 2000.
American Wood-Preservers' Association (AWPA) Standard A3-00, 2003.
Proceedings of the Fourth International Congress Pesticide Chemistry (IUPAC), Article VII-23, 1978.
Statutory Declaration of Dr. Robin Nicholas Wakeling, in the matter of Australian Patent Acceptance No. 2004230950 and Opposition thereto, dated Sep. 20, 2010.
Hungarian Search Report dated Jul. 15, 2010 for Singaporean Patent Application No. 200717645-6.
Australian Patent Office Examination Report dated Jun. 1, 2010 for Singaporean Patent Application No. 200717652-2.
Notice of Opposition to Grant of Patent (Section 21) (Application No. 542889) filed by Mattersmiths Holdings Limited on Jun. 22, 2010.
Ernest W. Flick, "Fungicides, Biocides and Preservatives for Industrial and Agricultural Applications," 1987, Noyes Publication, p. 184.

(56) References Cited

OTHER PUBLICATIONS

American Wood-Preservers' Association (AWPA) Standard E-11-97, pp. 1-3, 2003.
Opinion and Order dated Jan. 28, 2011, *Osmose, Inc.* v. *Arch Chemicals, Inc., et al.*, Civil Action No. 2:10 cv 108.
Expert Report of Dr. Frank Beall, Ph.d. Concerning the Invalidity of U.S. Pat. No. 7,674,481, U.S. District Court for the Eastern District of Virginia, Norfolk Division, Civil Action No. 2:10 cv 108.
Supplemental Expert Report of Dr. Frank Beall, Ph.D. Concerning the Invalidity of U.S. Pat. No. 7,674,481, Feb. 11, 2011, USDC Eastern District of Virginia, Norfolk Division, Civil Action No. 2:10cv108.
Rebuttal Expert Report of John Ruddick, USDC Eastern District of Virginia, Norfolk Division, Civil Action No. 2:10cv108. (Redacted).
American Wood Preservers' Association (AWPA) Standard E10-06, "Standard Method of Testing Wood Preservatives by Laboratory Soil-Block Cultures," 2007.
American Wood Preservers' Association (AWPA) Standard E10-09, "Standard Method of Testing Wood Perseverative by Laboratory Solid-Block Cultures," 2010.
American Wood Preservers' Association (AWPA) Standard E11-06, "Standard Method of Determining the Leachability of Wood Preservatives," 2007.
American Wood Preservers' Association (AWPA) Standard E22-09, "Standard Accelerated Laboratory Method for Testing the Efficacy of Preservatives Against Wood Decay Fungi Using Compression Strength," 2010.
ASTM D5664, "Standard Test Method for Evaluating the Effects of Fire-Retardant Treatments and Elevated Temperatures on Strength Properties of Fire Retardant Treated Lumber," 2002.
"Preservation of Timber with Zinc Chloride by the Steep Process," Technical Notes, Forest Products Laboratory, U.S. Forest Service.
Freeman, Mike et al. "A Comprehensive Review of Copper-Based Wood Preservatives," Forest Products Journal, vol. 58, No. 11, pp. 6-27, Nov. 2008.
Stirling, Rod, et al., "Micro-Distribution of Micronized Copper in Southern Pine," The International Research Group on Wood Protection, 39th Annual Meeting, May 25-28, 2008.

The Federal Circuit Bar Association Model Patent Jury Instructions.
Liese, W., "Fine Structure of Bordered Pits in Softwoods" Cellular Ultrastructure of Woody Plants, pp. 271-290, 1995.
Graph, "Fine Structure of Bordered Pits in Softwoods.".
Response to Office Action by Patent owner in inter Partes Reexamination under 37 CFR § 1.945, USPTO Reexamination Control No. 95/001,418, filed by Osmose, Inc., Dec. 21, 2010.
Third Party Comments after Patent Owner Response, USTPO Reexamination Control No. 95/001,418, filed by Arch Wood Protection, Inc., Jan. 20, 2011.
Liu, Y., et al., "Use of Nanoparticles for the Controlled Release of Biocides in Pressure-treated Solid Wood"; Presentation at the American Chemical Society, Las Vegas, Oct. 1997.
Amended Notice of Opposition to Grant of Patent (Section 21) and Statement of Case (Application No. 542889) filed by Mattersmiths Holdings Limited on Aug. 23, 2010; and Notice of Opposition to Grant of Patent (Section 21) (Application No. 542889) filed my Mattersmiths Holdings Limited on Jun. 22, 2010.
Request for Inter Partes Reexamination of U.S. Pat. No. 7,674,481 filed with the United States Patent and Trademark Office by Arch Wood Protection, Inc. on Aug. 13, 2010 and a draft of the Request.
First Office Action issued Oct. 21, 2010 in Inter Partes Reexamination Control No. 95/001,418.
Action Closing Prosecution issued Apr. 29, 2011 in Inter Partes Reexamination Control No. 95/001,418.
Dev et al., "Termite Resistance and Permanency Tests on Zinc-Borate—An Environmental Friendly Preservative," J. Timb. Dev. Assoc. (India) vol. XLIII, No. 2, Apr. 1997.
Laks et al., "Anti-sapstain efficacy of borates against *Aureobasidium pullulans*," Forest Products Journal 43(1): 33-34 (1993).
Shchigol, "Some Properities of Zinc and Cadmium Borates," Russian Journal of Inorganic Chemistry, 913-915 (1959).
Tsunoda, "Effects of zinc borate on the properties of medium density fiberboard. (Composites and Manufactured Products)," Forest Products Journal (Nov. 1, 2002).
Wang et al., "Treatability and durability of heartwood," in Ritter et al., eds., National Conference on Wood Transportation Structures, Oct. 23-25, 1995, Madison WI; Gen. Tech. Rep. FPL-GTR-94, Madison, WI: U.S.D.A. Forest Service, Forest Products Laboratory pp. 252-260 (1996).

\* cited by examiner

Coniferous Wood Anatomy

Bordered Pit

MICRONIZED WOOD PRESERVATIVE FORMULATIONS IN ORGANIC CARRIERS

This application claims priority to U.S. provisional application No. 60/618,729, filed on Oct. 14, 2004, the disclosure of which is hereby incorporated by reference.

FIELD OF THE INVENTION

The present invention pertains to wood preservation, and more specifically to the use of micronized metals, metal compounds, and organic biocides as wood preservatives.

BACKGROUND OF THE INVENTION

Wood preserving compositions are used to protect wood and other cellulose-based materials, such as paper, particleboard, textiles, rope, etc., from attack by wood-destroying organisms, such as, for example, fungi, bacteria and insects. Conventional wood preserving compositions often contain inorganic compounds, organic biocides, or both in an organic carrier. Examples of inorganic compounds used heretofore are compounds of copper, zinc, tin, boron, fluoride, etc. Organic biocides used heretofore include insecticides, fungicides, moldicides, algaecides, bactericides, etc. that have been dissolved in an oil-borne carrier. Examples of such compounds are azoles, carbamates, isothiazolinones, thiocyanates, sulfenamides, quaternary phosphonium compounds, quaternary ammonium compounds, nitriles, pyridines, etc. The preparation of such compounds in organic carriers is desirable because many organic carriers can impart water repellency and dimensional stability to cellulosic substrates such as wood. However, many inorganic compounds and organic biocides have limited solubility in common and desirable organic carriers, and heretofore, special measures have been taken to overcome the solubility hurdle. For example, inorganic compo have been added to organic carriers as organo-metallic compounds or have been complexed with an organic moiety to enhance its solubility characteristics in a desired organic carrier. Another technique which has been used is the formation of a water-in-oil emulsion in which compounds are dissolved in water as organo-metallic compounds, and the aqueous product is mixed with emulsifying compounds to produce the emulsion. However, these methods do not work for many desirable combinations of inorganic/organic component and organic solvent. Such solutions have remained difficult to prepare.

SUMMARY OF THE INVENTION

The present invention provides compositions and methods for preservation of wood. The composition comprises one or more micronized inorganic compounds, organic biocides, or both, and an organic carrier in which the micronized compounds are of low solubility. As used herein, the term inorganic compounds includes metal compounds, as well as inorganic complexes comprising one or more metal ions which are complexed with organic moieties.

A method is provided for the preparation of the composition. The method comprises the steps of providing an organic carrier and an inorganic compound, organic biocide, or both, which are insoluble in the organic carrier, and grinding them into micronized particles in the presence of dispersants and optionally, the carrier, such that a stable dispersion of micronized particles is formed. These compounds are ground by standard techniques known in the art. The inorganic compound/organic biocide particles have a size in the range of 0.001 microns to 25.0 microns.

The compositions of the present invention can be impregnated into cellulosic materials such as wood by standard methods, such as vacuum/pressure methods.

When such a composition is used for preservation of wood, there is often only minimal leaching if any, of the micronized component(s) upon exposure of the wood to the elements during use, particularly if the micronized component(s) have limited or no solubility in water.

DETAILED DESCRIPTION

Figure 1:
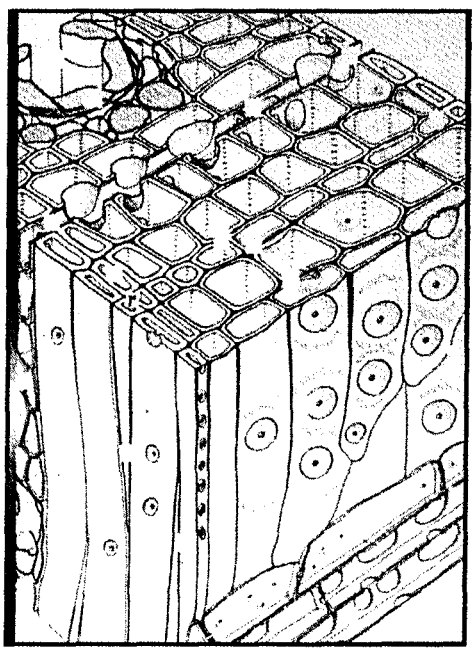
FIG. 1 depicts coniferous wood anatomy.

Disclosed herein is a micronized preservative composition, a method for its preparation, and method for its use thereof in the treatment of cellulosic material, especially wood. The leaching of metal element from the treated wood can be less than that observed with non-micronized compositions currently used in the art.

Metals or metal compounds which can be used in the micronized preservative compositions of the present invention in their elemental form or as compounds include transition elements (including the lanthanide and actinide series elements) such as strontium, barium, arsenic, antimony, bismuth, lead, gallium, indium, thallium, tin, zinc, cadmium, silver, nickel, etc. Such compounds should exhibit a relatively low solubility in the organic liquid which is to be used as a carrier.

A preferred metal is copper. Accordingly, in one embodiment, copper or copper compounds are used. The copper or copper compounds which can be used include cuprous oxide (a source of copper (I) ions), cupric oxide (a source of copper (II) ions), copper hydroxide, copper carbonate, basic copper carbonate, copper oxychloride, copper 8-hydroxyquinolate, copper dimethyldithiocarbamate, copper omadine, copper borate, and copper residues (e.g., copper metal byproducts).

Organic biocides such as fungicides, insecticides, moldicides, bactericides, algaecides etc. from chemical classes including azoles, carbamates, isothiazolinones, thiocyanates, sulfenamides, quaternary phosphonium compounds, quaternary ammonium compounds, nitriles, pyridines, etc. and mixtures thereof can be used with the present invention and are well known to those skilled in the art. The organic biocides used in the present invention may have varying degrees of solubility, depending upon the organic biocide and carrier which is used. The organic biocide may be either micronized or soluble in the carrier used, with the provision that if the composition does not contain a micronized metal/metal compound component, the organic biocide is present in the carrier as micronized particles. Some non-limiting examples of organic biocides are listed below.

TABLE I aliphatic nitrogen fungicides, such as, for example:

butylamine; cymoxanil; dodicin; dodine; guazatine; iminoctadine amide fungicides, such as, for example:

carpropamid; chloraniformethan; cyazofamid; cyflufenamid; diclocymet; ethaboxam; fenoxanil; flumetover; furametpyr; prochloraz; quinazamid; silthiofam; triforine; benalaxyl-M; furalaxyl; metalaxyl; metalaxyl-M; pefurazoate; benzohydroxamic acid; tioxymid; trichlamide; zarilamid; zoxamide; furmecyclox dichlofluanid; tolylfluanid benthiavalicarb; iprovalicarb; benalaxyl; benalaxyl-M; boscalid; carboxin; fenhexamid; metalaxyl; metalaxyl-M; metsulfovax; ofurace; oxadixyl; oxycarboxin; pyracarbolid; thifluzamide; tiadinil; benodanil; flutolanil; mebenil; mepronil; salicylanilide; tecloftalam fenfuram; furalaxyl; furcarbanil; methfuroxam flusulfamide antibiotic fungicides, such as, for example:

aureofungin; blasticidin-S; cycloheximide; griseofulvin; kasugamycin; natamycin; polyoxins; polyoxorim; streptomycin; validamycin; azoxystrobin; dimoxystrobin; fluoxastrobin; kresoxim-methyl; metominostrobin; orysastrobin; picoxystrobin; pyraclostrobin; trifloxystrobin aromatic fungicides, such as, for example:

biphenyl chlorodinitronaphthalene; chloroneb; chlorothalonil; cresol; dicloran; hexachlorobenzene; pentachlorophenol; quintozene; sodium pentachlorophenoxide; tecnazene benzimidazole fungicide, such as, for example:

benomyl; carbendazim; chlorfenazole; cypendazole; debacarb; fuberidazole; mecarbinzid rabenzazole; thiabendazole benzimidazole precursor fungicides, such as, for example:

furophanate; thiophanate; thiophanate-methyl benzothiazole fungicides, such as, for example:

bentaluron; chlobenthiazone; TCMTB bridged diphenyl fungicides, such as, for example:

bithionol; dichlorophen; diphenylamine carbamate fungicides, such as, for example:

benthiavalicarb; furophanat; e iprovalicarb; propamocarb; thiophanate; thiophanate-methyl;
benomyl; carbendazim; cypendazole; debacarb; mecarbinzid; diethofencarb conazole fungicides, such as, for example:

climbazole; clotrimazole; imazalil; oxpoconazole; prochloraz; azaconazole; triflumizole bromuconazole; cyproconazole; diclobutrazol; difenoconazole; diniconazole; diniconazole-M; epoxiconazole; etaconazole; fenbuconazole; fluquinconazole; flusilazole flutriafol; furconazole; furconazole-cis; hexaconazole; imibenconazole; ipconazole; metconazole; myclobutanil; penconazole; propiconazole; prothioconazole; quinconazole; simeconazole; tebuconazole; tetraconazole; triadimefon; triadimenol; triticonazole; uniconazole; uniconazole-P dicarboximide fungicides, such as, for example:

famoxadone; fluoroimide; chlozolinate; dichlozoline; iprodione; isovaledione; myclozolin; procymidone; vinclozolin; captafol; captan; ditalimfos; folpet; thiochlorfenphim dinitrophenol fungicides, such as, for example:

binapacryl; dinobuton; dinocap; dinocap-4; dinocap-6; dinocton; dinopenton; dinosulfon; dinoterbon; DNOC dithiocarbamate fungicides, such as, for example:

azithiram; carbamorph; cufraneb; cuprobam; disulfiram; ferbam; metam; nabam; tecoram thiram; ziram; dazomet; etem; milneb; mancopper; mancozeb; maneb; metiram polycarbamate; propineb; zineb imidazole fungicides, such as, for example:

cyazofamid; fenamidone; fenapani; l glyodin; iprodione; isovaledione; pefurazoate; triazoxide morpholine fungicides, such as, for example:

aldimorp; h benzamorf; carbamorph; dimethomorph; dodemorph; fenpropimorph; flumorph; tridemorph organophosphorus fungicides, such as, for example:

ampropylfos; ditalimfos; edifenphos; fosetyl; hexylthiofos; iprobenfos; phosdiphen; pyrazophos; tolclofos-methyl triamiphos oxathiin fungicides, such as, for example:

carboxin; oxycarboxin

TABLE I-continued oxazole fungicides, such as, for example:

chlozolinate; dichlozoline; drazoxolon; famoxadone; hymexazol; metazoxolon;
myclozolin; oxadixyl; vinclozolin
pyridine fungicides, such as, for example:

boscalid; buthiobate; dipyrithione; fluazinam; pyridinitril; pyrifenox; pyroxychlor;
pyroxyfur
pyrimidine fungicides, such as, for example:

bupirimate; cyprodinil; diflumetorim; dimethirimol; ethirimol; fenarimol; ferimzone;
mepanipyrim; nuarimol; pyrimethanil; triarimol
pyrrole fungicides, such as, for example:

fenpiclonil; fludioxonil; fluoroimide
quinoline fungicides, such as, for example:

ethoxyquin; halacrinate; 8-hydroxyquinoline sulfate; quinacetol; quinoxyfen;
quinone fungicides, such as, for example:

benquinox; chloranil; dichlone; dithianon
quinoxaline fungicides, such as, for example:

chinomethionat; chlorquinox; thioquinox
thiazole fungicides, such as, for example:

ethaboxam; etridiazole; metsulfovax; octhilinone; thiabendazole; thiadifluor; thifluzamide
thiocarbamate fungicides, such as, for example:

methasulfocarb; prothiocarb
thiophene fungicides, such as, for example:

ethaboxam; silthiofam
triazine fungicides, such as, for example:

anilazine
triazole fungicides, such as, for example:

bitertanol; fluotrimazole; triazbutil
urea fungicides, such as, for example:

bentaluron; pencycuron; quinazamid
Other fungicides, such as, for example:

acibenzolar; acypetacs; allyl alcohol; benzalkonium chloride; benzamacril; bethoxazin;
carvone; chloropicrin; DBCP; dehydroacetic acid; diclomezine; diethyl pyrocarbonate;
fenaminosulf; fenitropan; fenpropidin; formaldehyde; furfural; hexachlorobutadiene;
iodomethane; isoprothiolane; methyl bromide; methyl isothiocyanate; metrafenone;
nitrostyrene; nitrothal-isopropyl OCH; 2 phenylphenol; phthalide; piperalin; probenazole;
proquinazid; pyroquilon; sodium orthophenylphenoxide; spiroxamine; sultropen;
thicyofen; tricyclazole; methyl isothiocyanate
antibiotic insecticides, such as, for example:

allosamidin; thuringiensin; spinosad; abamectin; doramectin; emamectin; eprinomectin
ivermectin; selamectin; milbemectin; milbemycin oxime; moxidectin
botanical insecticides, such as, for example:

anabasine; azadirachtin; d-limonene; nicotine; pyrethrins; cinerins; cinerin I; cinerin II;
jasmolin; jasmolin II; pyrethrin I; pyrethrin II; quassia; rotenone; ryania; sabadilla
carbamate insecticides, such as, for example:

bendiocarb; carbaryl; benfuracarb; carbofuran; carbosulfan; decarbofuran; furathiocarb
dimetan; dimetilan; hyquincarb; pirimicarb; alanycarb; aldicarb; aldoxycarb;
butocarboxim; butoxycarboxim; methomyl; nitrilacarb; oxamyl; tazimcarb; thiocarboxime
thiodicarb; thiofanox; allyxycarb; aminocarb; bufencarb; butacarb; carbanolate;
cloethocarb; dicresyl; dioxacarb; EMPC; ethiofencarb; fenethacarb; fenobucarb;
isoprocarb; methiocarb; metolcarb; mexacarbate; promacyl; promecarb; propoxur;
trimethacarb; XMC; xylylcarb
dinitrophenol insecticides, such as, for example:

dinex; dinoprop; dinosam; DNOC; cryolite; sodium hexafluorosilicate; sulfluramid
formamidine insecticides, such as, for example:

amitraz; chlordimeform; formetanate; formparanate
fumigant insecticides, such as, for example:

acrylonitrile; carbon disulfide; carbon tetrachloride; chloroform; chloropicrin; para-
dichlorobenzene; 1,2-dichloropropane; ethyl formate; ethylene dibromide; ethylene TABLE I-continued dichloride; ethylene oxide; hydrogen cyanide; iodomethane; methyl bromide; methylchloroform; methylene chloride; naphthalene; phosphine; sulfuryl fluoride; tetrachloroethane
insect growth regulators, such as, for example:

bistrifluron; buprofezin; chlorfluazuron; cyromazine; diflubenzuron; flucycloxuron; flufenoxuron; hexaflumuron; lufenuron; novaluron; noviflumuron; penfluron; teflubenzuron; triflumuron; epofenonane; fenoxycarb; hydroprene; kinoprene; methoprene; pyriproxyfen; triprene; juvenile hormone I; juvenile hormone II; juvenile hormone III; chromafenozide; halofenozide; methoxyfenozide; tebufenozide; α-ecdysone; ecdysterone; diofenolan; precocene I; precocene II; precocene III; dicyclanil
nereistoxin analogue insecticides, such as, for example:

bensultap; cartap; thiocyclam; thiosultap; flonicamid; clothianidin; dinotefuran; imidacloprid; thiamethoxam; nitenpyram; nithiazine; acetamiprid; imidacloprid; nitenpyram; thiacloprid
organochlorine insecticides, such as, for example:

bromo-DDT; camphechlor; DDT; pp'-DDT; ethyl-DDD; HCH; gamma-HCH; lindane; methoxychlor; pentachlorophenol; TDE; aldrin; bromocyclen; chlorbicyclen; chlordane; chlordecone; dieldrin; dilor; endosulfan; endrin; HEOD; heptachlor; HHDN; isobenzan; isodrin; kelevan; mirex
organophosphorus insecticides bromfenvinfos; chlorfenvinphos; crotoxyphos; dichlorvos; dicrotophos; dimethylvinphos; fospirate; heptenophos; methocrotophos; mevinphos; monocrotophos; naled; naftalofos; phosphamidon; propaphos; schradan; TEPP; tetrachlorvinphos; dioxabenzofos; fosmethilan; phenthoate; acethion; amiton; cadusafos; chlorethoxyfos; chlormephos; demephion; demephion-O; demephion-S; demeton; demeton-O; demeton-S; demeton-methyl; demeton-O-methyl; demeton-S-methyl; demeton-S-methylsulphon; disulfoton; ethion; ethoprophos; IPSP; isothioate; malathion; methacrifos; oxydemeton-methyl; oxydeprofos; oxydisulfoton; phorate; sulfotep; terbufos; thiometon; amidithion; cyanthoate; dimethoate; ethoate-methyl; formothion; mecarbam; omethoate; prothoate; sophamide; vamidothion; chlorphoxim; phoxim; phoxim-methyl; azamethiphos; coumaphos; coumithoate; dioxathion; endothion; menazon; morphothion; phosalone; pyraclofos; pyridaphenthion; quinothion; dithicrofos; thicrofos; azinphos-ethyl; azinphos-methyl; dialifos; phosmet; isoxathion; zolaprofos; chlorprazophos; pyrazophos; chlorpyrifos; chlorpyrifos-methyl; butathiofos; diazinon; etrimfos; lirimfos; pirimiphos-ethyl; pirimiphos-methyl; primidophos; pyrimitate; tebupirimfos; quinalphos; quinalphos-methyl; athidathion; lythidathion; methidathion; prothidathion; isazofos; triazophos; azothoate; bromophos; bromophos-ethyl; carbophenothion; chlorthiophos; cyanophos; cythioate; dicapthon; dichlofenthion; etaphos; famphur; fenchlorphos; fenitrothion; fensulfothion; fenthion; fenthion-ethyl; heterophos; jodfenphos; mesulfenfos; parathion; parathion-methyl; phenkapton; phosnichlor; profenofos; prothiofos; sulprofos; temephos; trichlormetaphos-3; trifenofos; butonate; trichlorfon; mecarphon; fonofos; trichloronat; cyanofenphos; EPN; leptophos; crufomate; fenamiphos; fosthietan; mephosfolan; phosfolan; pirimetaphos; acephate; isocarbophos; isofenphos; methamidophos; propetamphos; dimefox; mazidox; dimefox; mazidox; mipafox
oxadiazine insecticides, such as, for example:

indoxacarb
phthalimide insecticides, such as, for example:

dialifos; phosmet; tetramethrin
pyrazole insecticides, such as, for example:

acetoprole; ethiprole; fipronil; tebufenpyrad; tolfenpyrad; vaniliprole
pyrethroid insecticides, such as, for example:

acrinathrin; allethrin; bioallethrin; barthrin; bifenthrin; bioethanomethrin; cyclethrin; cycloprothrin; cyfluthrin; beta-cyfluthrin; cyhalothrin; gamma-cyhalothrin; lambda-cyhalothrin; cypermethrin; alpha-cypermethrin; beta-cypermethrin; theta-cypermethrin; zeta-cypermethrin; cyphenothrin; deltamethrin; dimefluthrin; dimethrin; empenthrin; fenfluthrin; fenpirithrin; fenpropathrin; fenvalerate; esfenvalerate; flucythrinate; fluvalinate; tau-fluvalinate; furethrin; imiprothrin; permethrin; metofluthrin; biopermethrin; transpermethrin; phenothrin; prallethrin; profluthrin; pyresmethrin; resmethrin; bioresmethrin; cismethrin; tefluthrin; terallethrin; tetramethrin; tralomethrin; transfluthrin; etofenprox; flufenprox; halfenprox; protrifenbute; silafluofen
pyrimidinamine insecticides, such as, for example:

flufenerim; pyrimidifen
pyrrole insecticides, such as, for example:

chlorfenapyr
tetronic acid insecticide, such as, for example:

spiromesifen
thiourea insecticides, such as, for example:

diafenthiuron

TABLE I-continued urea insecticide, such as, for example:

flucofuron; sulcofuron
Other insecticides, such as, for example:

closantel; crotamiton; EXD; fenazaflor; fenoxacrim; hydramethylnon; isoprothiolane; malonoben; metoxadiazone; nifluridide; pyridaben; pyridalyl; rafoxanide; triarathene; triazamate
Bactericides, such as, for example:

bronopol, cresol, dichlorophen, dipyrithione; dodicin; fenaminosulf; formaldehyde; hydrargaphen; 8-hydroxyquinoline sulfate; kasugamycin; nitrapyrin; octhilinone; oxolinic acid; oxytetracycline; probenazole; streptomycin; tecloftalam; thiomersal The ambit of the present invention includes the use of the above compounds and biocides in micronized form. The term "micronized" as used herein means a particle size in the range of 0.001 to 25 microns. The term "particle size" refers to the largest axis of the particle, and in the case of a generally spherical particle, the largest axis is the diameter. The micronized particles can be obtained by wetting/dispersing and grinding the inorganic compounds, with or without organic carriers, using a grinding mill. However, it should be understood that "micronized" does not refer only to particles which have been produced by the finely dividing, such as by mechanical grinding, of materials which are in bulk or other form, but to particles in the foregoing size range, whether they are ground from larger stock, precipitated out of solution, formed using nanotechnological methods, formed in situ, etc.

It is preferred that the particles be formed in the presence of dispersants, such as stabilizers, wetting agents, surfactants, etc., such that a stable particle dispersion is formed. Standard dispersants can be used, such as acrylic copolymers, polymers with pigment affinic groups or other modifications which give them affinity for the micronized component(s) ("modified"). Other dispersants are modified polyacrylate, acrylic polymer emulsions, modified lignin, organically modified polysiloxane, modified polyurethane, polycarboxylate ether, modified fatty acids and fatty acid esters, modified polyether, modified polyamides, and the like.

A "dispersion" of micronized particles should be interpreted to encompass situations in which particles are present with sizes outside the micronized range. However, it is preferred that greater than 80 wt % of the particles have diameters in the micronized range, and even more preferred that greater than 60 wt % of the micronized particles have a size of between 0.05 to 1.0 microns.

All embodiments contain at least one metal/metal compound or organic biocide which is present as a micronized dispersion. When the composition comprises both types of components, either can be present in micronized form. In one embodiment, both the inorganic compound component and the organic biocide component are present as micronized particles.

For the purposes herein, an inorganic compound or an organic biocide component will generally be considered to have the ability to be present in a wood preservative solution as micronized particles (i.e., little or no dissolution in the carrier), if the compound has a solubility in the organic carrier of less than or equal to 0.5 g per 100 grams of carrier at 25° C. More preferred is a solubility of less than or equal to 0.1 g per 100 grams of carrier at 25° C.

The compositions of the present invention can be prepared and stored as a concentrate, if desired, which can be diluted with an appropriate reconstituent to give a solution having a desired concentration of micronized component for applying to wood. Included within the ambit of the present invention are situations in which the organic carrier used to reconstitute a concentrate solution is different from the organic carrier which is present in the concentrate. Such a situation may arise, for example, if further dilution with the same organic carrier which is in the concentrate would cause appreciable dissolution of the micronized inorganic component. A second organic carrier may have properties which are more suited to the application for which the composition is to be used than the carrier which makes up the concentrate.

Compositions which contain extremely high weight percent of micronized particles may be of high viscosity, and such solutions may require measures such as high pressures to ensure penetration. However, viscosity of the composition is dependent upon the chosen carrier as well as the identity of the micronized component, and it is within the abilities of one skilled in the art to dilute or otherwise reduce the concentration of micronized component if excessive viscosity prevents or inhibits penetration. As a rule, solutions having a micronized particle wt % in excess of 50 wt % may require the use of high pressures to achieve significant penetration. However, a solution which is a concentrate which is intended for dilution before use may have a wt % of micronized particles which is even higher than 50 wt %.

In general, the wood preservative solution can have a micronized particle wt % as high as 85 wt % or as low as 0.00001 wt %, although for some applications, concentrations outside this range may be appropriate. The foregoing range includes both ready-to-apply solutions and concentrates.

In the compositions of the present invention it can be desirable to use components in addition to the inorganic compound, organic biocide and organic carrier components in order to enhance the performance of the wood preservative solution. Such components may be used as dispersants, defoamers, weathering agents, colorants, etc.

The preservative solutions of the present invention can be prepared in a variety of ways. The component or components which are to be present as micronized particles in the preservative solution (the "solid component") can be added to the carrier as a dispersion of micronized particles in a liquid phase, or they can be added to the carrier as large particulate or other solid form before grinding the particles to micronized size, preferably in the presence of dispersants. Solid components can be added as large particulate for later grinding, or as micronized particulate. If desired, micronized solids can be added directly to a carrier which contains a dispersant. The micronized particles can be obtained by grinding a metal/metal compounds or organic biocide component in the presence of a wetting agent and/or a dispersant using a commercially available grinding mill in the absence or presence of a solution. It is convenient to grind the particles in the presence of a carrier and a dispersant such that the suspension is formed in the carrier without the additional step of adding the dispersion to the carrier. Alternatively, micronized compounds may also be purchased from commercial sources and, if needed, ground further, optionally in the absence of the carrier.

The micronized compounds and biocides in an organic carrier can form a finely dispersed suspension with or without addition of a thickener. The resulting dispersion can optionally be mixed with a variety of biocides which are soluble in the carrier.

For preparing the compositions of the present invention, the soluble components can be added to the organic carrier prior to, during or after the micronization of the components. In one embodiment, micronized particles can be first made (by any suitable means) and then dispersed in the carrier. Other compounds and biocides, such as organic or inorganic biocides, soluble or insoluble, can be added to the dispersion, if desired.

Heretofore, technology has typically required the addition of an organic co-solvent or chelating agent to solubilize or complex the copper or other inorganic or organic biocides into an organic carrier. Disadvantages of the typical approach used in the art include the limited number of inorganic and/or organic biocides that are suitable for use in the standard organic solvent systems currently accepted by the wood preserving industry. Some biocides would require solvents that have dangerously low flash points or have significant health or environmental hazards associated with their use. Furthermore, using current technologies, metal or biocide components may be prone to leaching. The use of the present invention allows the addition of a variety of inorganic and organic biocides to carrier systems which comply with the Standard P9 (Standards for Solvents and Formulations for Organic Preservative Systems) of the American Wood Preservers Association.

This invention also allows the addition of performance enhancing non-biocidal products such as water repellants, colorants, emulsifying agents, dispersants, stabilizers, UV inhibitors, drying agents, polymer systems and the like disclosed herein to further enhance the performance of the system or the appearance and performance of the resulting treated products.

The ambit of the present invention includes the use of a wide range of organic carriers. Non-limiting examples of organic carriers that can be used, either alone, or as mixtures, as solubility allows, include:

Amines such as, for example: Diamylamine, Diethylamine, Diisopropylamine, Dimethylethylamine, Di-n-Butylamine, Mono-2-Ethylhexyamine, Monoamylamine, Monoethylamine 70%, Monoisopropylamine, Anhy., Mono-n-Butylamine, Triamylamine, Triethylamine, Tri-n-Butylamine, Dibutylaminoethanol, Diethylaminoethanol, Diethylaminoethoxyethanol, Diisopropylaminoethanol, Dimethylamino-2P, 77% Mixed, Dimethylamino-2-P, Anhy., Dimethylaminoethanol, Dimethylaminoethoxyethanol, Ethylaminoethanol, Ethylaminoethanol, Mixed, Isopropylaminoethanol, Isopropylaminoethanol, Mixed, Methyldiethanolamine, Monomethylaminoethanol, Mono-n-Propylaminoethanol, n-Butylaminoethanol, n-Butyldiethanolamine, Photo, t-Butylaminoethanol, t-butyldiethanolamine, Diethanolamine, Monoethanolamine, Triethanolamine, Triethanolamine 85%/99%, Diisopropanolamine, Monoisopropanolamine, Triisopropanolamine, Aminoethylethanolamine, Aminoethylpiperazine, Diethylenetriamine, Ethylenediamine, Piperazine 65%/Anhy., Piperazine, Tetraethylenepentamine, Triethylenetetramine, 3-Methoxypropylamine, AMP® Regular/95, Cyclohexylamine, Morpholine, Neutrol TE®;

Glycols, such as, for example: Diethylene Glycol, Dipropylene Glycol, Ethylene Glycol, Glycerine 96%, 99%, U.S.P., Glycerine, Hexylene Glycol, Neol® Neopentyiglycol, Polyethylene Glycol, Polypropylene Glycol, Propylene Glycol Ind., U.S.P., Tetraethylene Glycol, Triethylene Glycol, Tripropylene Glycol;

Ketones such as, for example: Acetone, Cyclohexanone, Diacetone, DIBK—Diisobutyl Ketone, Isophorone, MAK—Methyl Amyl Ketone, MEK—Methyl Ethyl Ketone, MIAK—Methyl Isoamyl Ketone, MIBK—Methyl Isobutyl Ketone, MPK—Methyl Propyl Ketone;

Esters such as, for example: Amyl Acetate, Dibasic Ester, Ethyl Acetate, 2 Ethyl Hexyl Acetate, Ethyl Propionate, Exxate® Acetate Esters, Isobutyl Acetate, Isobutyl Isobuterate, Isopropyl Acetate, n-Butyl Acetate, n-Butyl Propionate, n-Pentyl Propionate, n-Propyl Acetate;

Alcohols such as, for example: Amyl Alcohol, Benzyl Alcohol, Cyclohexanol, Ethyl Alcohol-Denatured, 2-Ethyl Hexanol, Exxal 8® Isooctyl Alcohol, Exxal 10® Isodecyl Alcohol, Exxal 13® Tridecyl Alcohol, Furfuryl Alcohol, Isobutyl Alcohol, Isopropyl Alcohol 99% Anhy, Methanol, Methyl Amyl Alcohol (MIBC), n-Butyl Alcohol, n-Propyl Alcohol, Neodol® Linear Alcohol, Secondary Butyl Alcohol, Tertiary Butyl Alcohol, Tetrahydrofurfuryl Alcohol, Texanol Ester Alcohol®, UCAR Filmer IBT®;

Halogenated Carriers such as, for example: Methylene Chloride, Monochlorobenzene, Orthodichlorobenzene, Perchloroethylene, Trichloroethylene, Vertrel® Hydrofluorocarbon;

Aliphatic Carriers such as, for example: Heptane, Hexane, Kerosene, Lacquer Diluent, Mineral Seal Oil, Mineral Spirits, n-Pentane, OMS-Odorless Mineral Spirits, Rubber Solvent, 140 Solvent, 360 Solvent, Textile Spirits®, VM&P;

Aromatic Carriers such as, for example: Aromatic 100, Aromatic 150, Aromatic 200, Heavy Aromatic Solvent, Panasol®, Toluene, Xylene;

Terpene Carriers such as, for example: Alpha-Pinene, Wood, Dipentene 122®, D-Limonene, Herco® Pine Oil, Solvenol®, Steam Distilled Turpentine, Terpineol®, Yarmor® 302,302-W Pine Oil;

Other carriers, including, for example: mineral oil, linseed oil, olive oil, vegetable oil, methoxypropyl acetate, isopropyl alcohol, castor oil, Arconate HP® Propylene Carbonate, #2 fuel oil, Cypar® Cycloparaffin Solvent, DMF—dimethyl formamide, formamide, Exxprint® Ink Oil/Solvent, furfural, Isopar® Isoparaffin Solvent, MTBE—methyl tert-butyl ether, NMP—N-methyl pyrrolidone, Norpar® Normal Paraffin Solvent, Proglyde DMM® Glycol Diether, THF—tetrahydrofuran, Varsol® Aliphatic Solvent.

Figure 2:
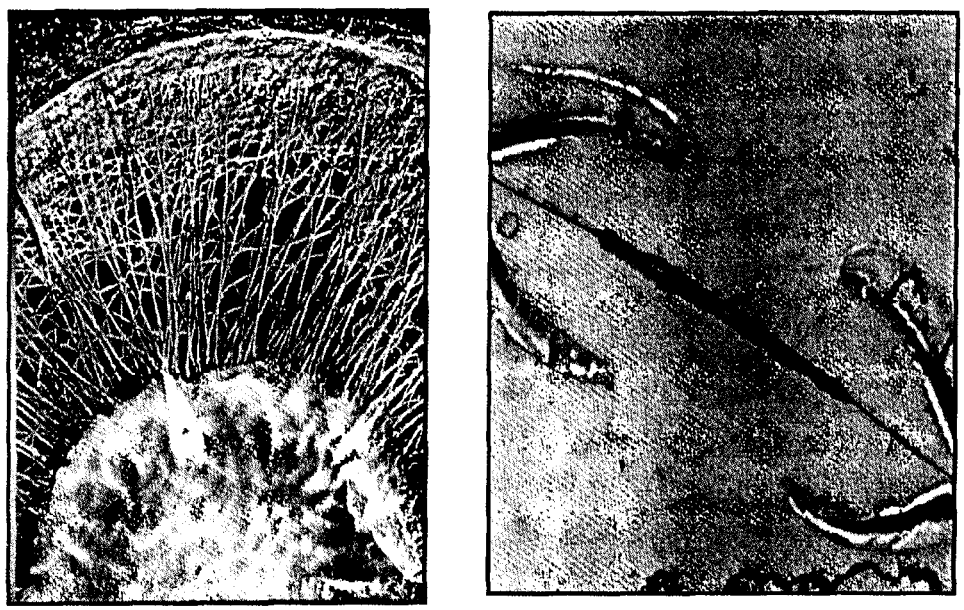
FIG. 2 depicts the border pit structure for coniferous woods.

Also important is the penetration of the dispersed formulation into the cellular structure of the wood or other cellulose-based material. If the solids used in formulating the dispersion formulation disclosed herein have a particle size in excess of 30 microns, the particles may be filtered by the surface of the wood and thus may not be uniformly distributed within the cell and cell wall. FIG. 1 depicts the anatomy of coniferous wood. As shown in FIG. 2, the primary entry and movement of fluids through wood tissue occurs primarily through the tracheids and border pits. Tracheids have a diameter of about thirty microns. Fluids are transferred between wood cells by means of border pits.

The overall diameter of the border pit chambers typically varies from a several microns up to thirty microns while, the diameter of the pit openings (via the microfibrils) typically varies from several hundredths of a micron to several microns. FIG. 2 depicts the border pit structure for coniferous woods.

Particle sizes of the metal or low water solubility organic biocide used in the composition which exceed 30 microns tend to be filtered by the surface of the wood, thus not attaining a desired penetration and fluid flow through the wood tissue.

In one embodiment particle size of the micronized particles used in the dispersion formulation disclosed herein can have a long axis dimension ("size") between 0.001-25 microns. In another embodiment, the particle size is between 0.001-10 microns. In another embodiment, the particle size is between 0.01 to 10 microns. If superior uniformity of penetration is desired, particle size of the additive used in the dispersion formulation disclosed herein should be between 0.01-1 microns.

In addition to a recommended upper limit of 25 microns, Particles which are too small can leach out of the wood over time. It is thus generally recommended that the particulate additive comprise particles which have diameters which are not less than 0.001 microns.

Particles which are too large can clog the wood, preventing it from taking in other particles and particles which are too small can leach from the wood. Thus particle size distributional parameters can affect the uniformity of particle distribution in the wood, as well as the leaching properties of treated wood. It is thus preferable to use particle size distributions which contain relatively few particle sizes outside the range of 0.001 to 25 microns. It is preferred that no more than 20 weight percent of the particles have diameters which are greater than 25 microns. Because smaller particles have an increased chance of leaching from the wood, it is also preferred that no more than 20 wt % of the particles have diameters under 0.001 microns. Regardless of the foregoing recommendations, it is generally preferred that greater than 80 wt % of the particles have a diameter in the range of 0.001 to 25 microns. In more preferred embodiments, greater than 85, 90, 95 or 99 wt % particles are in the range of 0.001 to 25 microns.

For increased degree of penetration and uniformity of distribution, at least 50 wt % of the particles should have diameters which are less than 10 microns. More preferred are particle distributions which have at least 65 wt % of the particles with sizes of less than 10 microns. In additional embodiments, less than 20 wt % of the particles have diameters of less than 1 micron.

The following examples are provided to further describe certain embodiment of the disclosure but are in no way limiting to the scope of disclosure. Examples 1 through 5 demonstrate the formulation of the concentrated dispersions of copper compounds, copper compounds and various organic biocides, or organic biocides in an organic carrier. Examples 6 through 13 demonstrate the preparation and use of treating fluids containing micronized dispersions for the treatment of wood.

EXAMPLE 1

This example demonstrates the preparation of a dispersion of a micronized metal compound according to the present invention. Five hundred (500.0) grams of copper hydroxide were added to a container containing 1091.7 grams white mineral spirits and 125.0 grams of dispersants/wetting agents. The mixture was mechanically stirred for 5 minutes and then placed in a grinding mill. The sample was ground for about 30 minutes, and a stable dispersion containing about 30 wt % copper hydroxide was obtained with an average particle size of 0.195 micrometers.

EXAMPLE 2

This example demonstrates the preparation of a dispersion of a micronized metal compound according to the present invention. One thousand (1000.0) grams of basic copper carbonate was mixed with 2158.3 grams of #2 fuel oil and 175.0 grams of wetting agents/dispersants. The mixture was mechanically stirred for 10 minutes. The mixture was then placed in a grinding mill and ground for about 20 minutes. A stable dispersion was obtained with an average particle size of 0.199 micrometers.

EXAMPLE 3

This example demonstrates the preparation of a dispersion containing a micronized metal compound and a micronized organic biocide according to the present invention. One thousand (1000.0) grams of basic copper hydroxide and 20 grams of tebuconazole were mixed with 3780 grams of mineral spirits and 200 grams of wetting agents/dispersants. The mixture was mechanically stirred for about 10 minutes. The mixture was then placed in a grinding mill and ground for about 30 minutes. A stable dispersion containing 25 wt % basic copper carbonate and 0.5 wt % tebuconazole was obtained with an average particle size of 0.200 micrometers.

EXAMPLE 4

This example demonstrates the preparation of a dispersion of a micronized metal compound according to the present invention. Three hundred (300) grams of copper 8-hydroxyquinolate (Cu-8) were mixed with 855 grams n-butyl acetate and 90.0 grams of dispersants. The mixture was mechanically mixed for about 5 minutes and placed in a grinding mill. The mixture was ground for about 30 minutes and a stable dispersion containing 25 wt % Cu-8 was obtained with an average particle size of 0.282 micrometers.

EXAMPLE 5

Five hundred (500.0) grams of tebuconazole and 80.0 grams of bifenthrin were mixed with 800.0 g of #2 fuel oil and 300.0 g of dispersants. The mixture was mechanically mixed for about 10 minutes and then transferred into a grinding mill. The mixture was ground for about 45 minutes and a stable dispersion was achieved with a concentration of tebuconazole of 29.8 wt % and bifenthrin of 4.8 wt %.

EXAMPLE 6

This example demonstrates the uniform penetration achievable with the preservative compositions of the present invention. The cupric hydroxide dispersion from Example 1 (38.5 g) was mixed with 7.5 g of N, N-dimethyl-1-dodecylamine-N-oxide (AO) and 2954.0 g of mineral spirits to produce a preservative treating fluid containing 0.385 wt % cupric hydroxide and 0.25 wt % AO. The fluid was then used to treat 2"×4"×10" samples of southern pine sapwood using an initial vacuum of 28" Hg for 15 minutes, followed by a pressure cycle of 135 psi for 25 minutes and a final vacuum of 27" Hg for 10 minutes. The resulting treated wood was weighed and found to have doubled its weight. Treated sample was cut and the cross sections sprayed with a copper indicator to determine copper penetration following the procedure described in American Wood Preservers' Association Standard A3-00, and the blue color indicates the presence of copper.

EXAMPLE 7

This example demonstrates the uniform penetration achievable with the preservative compositions of the present invention. Fifty (50.0) g basic copper carbonate dispersion from Example 3 were mixed with 2942.5 g of mineral spirits and 7.5 g of didecyldimethylammonium chloride. The product was mixed until uniformly dispersed and the treating solution containing the following compositions:

| Components | Percent |
| --- | --- |
| Cupric Oxide | 0.50 |
| Didecyldimethylammonium Chloride | 0.25 |

A southern pine stake measuring 1.5"×3.5"×10" was placed in a laboratory retort with a vacuum of 27" Hg for 15 minutes. The treating solution was then pumped into the retort and the retort pressurized to 130 psi for 30 minutes. The solution was drained from the retort and the test stake weighed. Based on the weight pickup, the test stake doubled its weight and showed uniform penetration of the cupric oxide throughout the wood cross section.

EXAMPLE 8

This example demonstrates the uniform penetration achievable with the preservative compositions of the present invention, as well as their ability to preserve wood. A preservative treating formulation was prepared by adding 0.15 kg of copper carbonate dispersion from Example 2 to 0.025 kg of N, N-dimethyl-1-hexadecylamine-N-oxide and 4.825 kg of #2 fuel oil. This fluid was allowed to mix until a homogenous fluid was prepared. This fluid was used to treat southern pine test stakes by the full-cell process. The resulting stakes showed a uniform distribution of copper throughout the wood cells and were found to be resistant to decay and insect attack.

EXAMPLE 9

This example demonstrates the uniform penetration achievable with the preservative compositions of the present invention, as well as their ability to preserve wood. A preservative treating composition was prepared by adding 0.1 kg of dispersion from Example 3 to 4.9 kg of #2 fuel oil. The resulting fluid contained 0.50 wt % copper hydroxide and 0.01 wt % tebuconazole. This fluid was then used to treat full-size lumber using the full-cell process wherein the wood is initially placed under a vacuum of 30" Hg for 30 minutes, followed by the addition of the treating solution. The system was then pressurized for 30 minutes at 110 psi. A final vacuum of 28" Hg for 30 minutes is applied to the wood to remove residual liquid. The wood is found to contain a uniform distribution of copper throughout the cross sections and is resistant to fungal and insect attack.

EXAMPLE 10

This example demonstrates the uniform penetration achievable with the preservative compositions of the present invention, as well as their ability to preserve wood. Fifty-four grams of dispersion from Example 3 and 7.5 g of N, N-dimethyl-1-hexadecylamine-N-oxide (AO) (an organic biocide) were mixed with 2938.5 grams of # 2 fuel oil to obtain a preservative treating fluid containing 0.45% copper hydroxide, 0.009 wt % tebuconazole and 0.25 wt % AO. The resulting fluid is used to treat red pine lumber using a modified full-cell process. The resulting stakes are air-dried and found to a uniform distribution of copper throughout the cross sections and are resistant to fungal and insect attack.

EXAMPLE 11

This example demonstrates the uniform penetration achievable with the preservative compositions of the present invention, as well as their ability to preserve wood. This example also demonstrates the reconstitution of a concentrate containing an organic carrier which is different than the organic carrier which is used to reconstitute. A preservative treating fluid was prepared by adding 16.0 g of Cu 8-hydroxyquinolate (Cu-8) dispersion from Example 4 to 3984.0 g of #2 fuel oil. The resulting fluid contained 0.1 wt % Cu-8. The fluid was used to treat southern pine lumber using a full cell process. The treated stakes are oven dried and found to contain a uniform distribution of particles throughout the cross sections and are resistant to fungal and insect attack.

EXAMPLE 12

This example demonstrates the uniform penetration achievable with the preservative compositions of the present invention, as well as their ability to preserve wood. A preservative treating fluid was prepared by mixing 175 g concentrated dispersion containing 20 wt % copper carbonate and 0.5 wt % cyproconazole with 3325.0 g methoxypropyl acetate. The resulting solution contains 1.0% copper carbonate and 0.025% cyproconazole and is used to treat southern pine lumber using a full cell process. The treated stakes are oven dried and found to contain a uniform distribution of copper and cyproconazole throughout the cross sections and are resistant to fungal and insect attack.

EXAMPLE 13

A preservative treating fluid was prepared by mixing 1.70 g concentrate from Example 5 with 998.3 g of #2 fuel oil. The resulting solution contains 0.05 wt % tebuconazole and 0.008 wt % bifenthrin is used to treat southern pine lumber using a full cell process. The treated stakes are oven dried and the exposed to fungal species and Formosan subterranean termite. The testing results indicate that the treated wood is resistant to fungal and insect attack.

We claim:
1. A method for preserving a wood product comprising the step of contacting the wood product with an organic liquid wood preservative composition consisting essentially of:
    (a) a carrier consisting essentially of one or more liquid organic components;
    (b) solid particles of copper and/or one or more copper compounds dispersed in said one or more organic liquid components;
    wherein the solid particles have a solubility in the carrier of less than or equal to 0.5 gram per 100 grams of carrier at 25° C., and greater than 80 weight percent of the solid particles have a diameter in the range of 0.001 to 25 microns; and wherein at least 50 weight percent of the solid particles have diameters less than 10 microns; and wherein less than 20 weight percent of the solid particles have diameters less than 0.001 micron; and (c) an organic biocide.

2. The method of claim 1, wherein greater than 85 weight percent of the solid particles have a diameter in the range of 0.001 to 25 microns.

3. The method of claim 2, wherein greater than 90 weight percent of the solid particles have a diameter in the range of 0.001 to 25 microns.

4. The method of claim 3, wherein greater than 95 weight percent of the solid particles have a diameter in the range of 0.001 to 25 microns.

5. The method of claim 4, wherein greater than 99 weight percent of the solid particles have a diameter in the range of 0.001 to 25 microns.

6. The method of claim 1, wherein the solid particles have a solubility in the carrier of less than or equal to 0.1 gram per 100 grams of carrier at 25° C.

7. The method of claim 1, wherein the copper and/or the one or more copper compounds comprise copper hydroxide, copper oxide, copper carbonate, basic copper carbonate, copper oxychloride, copper 8-hydroxyquinolate, copper dimethyldithiocarbamate, copper omadine or copper borate.

8. The method of claim 1, wherein the organic biocide comprises a fungicide, insecticide, moldicide, bactericide, or algaecide, or combinations thereof.

9. The method of claim 1, further comprising the step of diluting the composition before the contacting step, wherein the composition is a concentrate before the diluting step.

10. The method of claim 1, wherein the composition is a treating solution.

11. The method of claim 1, wherein the one or more liquid organic components are selected from the group consisting of white mineral spirits, #2 fuel oil, n-butyl acetate, methoxypropyl acetate, toluene, xylene, linseed oil, mineral oil, olive oil, vegetable oil, castor oil and mineral spirits.

12. The method of claim 1, wherein the composition further comprises one or more dispersants and/or wetting agents.

13. The method of claim 1, wherein the composition further comprises one or more surfactants, defoamers, weathering agents, water repellants, colorants, emulsifying agents, stabilizers, UV inhibitors, drying agents and/or polymer systems.

* * * * *